(12) United States Patent
Elton et al.

(10) Patent No.: US 10,105,522 B2
(45) Date of Patent: Oct. 23, 2018

(54) RADIOPAQUE MEDICAL BALLOON

(75) Inventors: Richard K. Elton, Queensbury, NY (US); Corey E. Stapleton, Gilbert, AZ (US)

(73) Assignee: C.R. BARD, INC., Tempe, AZ (US)

( * ) Notice: Subject to any disclaimer, the term of this patent is extended or adjusted under 35 U.S.C. 154(b) by 822 days.

(21) Appl. No.: 14/123,596

(22) PCT Filed: Jun. 4, 2012

(86) PCT No.: PCT/US2012/040660
§ 371 (c)(1),
(2), (4) Date: Dec. 3, 2013

(87) PCT Pub. No.: WO2012/167220
PCT Pub. Date: Dec. 6, 2012

(65) Prior Publication Data
US 2014/0336689 A1    Nov. 13, 2014

Related U.S. Application Data

(60) Provisional application No. 61/533,411, filed on Sep. 12, 2011, provisional application No. 61/493,176, filed on Jun. 3, 2011.

(51) Int. Cl.
*A61M 25/10* (2013.01)
*A61B 90/00* (2016.01)
*A61B 17/22* (2006.01)

(52) U.S. Cl.
CPC . *A61M 25/104* (2013.01); *A61B 2017/22001* (2013.01); *A61B 2090/3966* (2016.02);
(Continued)

(58) Field of Classification Search
CPC ............ A61M 25/104; A61M 25/1002; A61M 25/10; A61M 2205/32; A61M 2025/1079;
(Continued)

(56) References Cited

U.S. PATENT DOCUMENTS 5,531,721 A * 7/1996 Pepin et al. .................. 604/525
6,652,568 B1   11/2003 Becker et al.
(Continued)

FOREIGN PATENT DOCUMENTS

EP          0775500 A1    5/1997
WO       2010027998 A1    3/2010

*Primary Examiner* — Eric Rosen
*Assistant Examiner* — Mikail Mannan
(74) *Attorney, Agent, or Firm* — King & Schickli, PLLC

(57) ABSTRACT

A medical balloon is made radiographic, such as by incorporating a radiopaque foil or film layer. The radiopaque foil or film layer may be placed between an inner layer and an outer layer of a non-compliant balloon wall. The foil or film may provide the balloon with a radiographic quality from a first end to a second end in the absence of an inflation fluid. The balloon may be provided with the foil or film in a manner that provides a first section, such as the barrel, with a first radiographic quality, and a second section, such as the cone, with a second radiographic quality. The film may also be applied as a decal or appliqué to the external surface of a balloon-shaped body. Related methods are also disclosed.

19 Claims, 9 Drawing Sheets

(52) U.S. Cl.
CPC ............... *A61M 2025/1075* (2013.01); *A61M 2025/1079* (2013.01); *A61M 2205/32* (2013.01); *A61M 2210/12* (2013.01)

(58) Field of Classification Search
CPC ...... A61M 2025/1075; A61M 2210/12; A61B 17/12136; A61B 17/12109
USPC ........................................................ 606/194
See application file for complete search history.

(56) References Cited

U.S. PATENT DOCUMENTS

| | | | |
|---|---|---|---|
| 6,911,017 B2 | 6/2005 | Lee et al. | |
| 6,942,688 B2* | 9/2005 | Bartholf et al. | 623/1.11 |
| 2006/0058867 A1 | 3/2006 | Thistle et al. | |
| 2006/0085022 A1 | 4/2006 | Hayes et al. | |
| 2008/0021495 A1 | 1/2008 | Lee et al. | |
| 2009/0299327 A1* | 12/2009 | Tilson et al. | 604/500 |
| 2010/0234875 A1* | 9/2010 | Allex et al. | 606/194 |

* cited by examiner

RADIOPAQUE MEDICAL BALLOON

This application claims the benefit of U.S. Provisional Patent Application Ser. Nos. 61/493,176 and 61/533,411, the disclosures of which are incorporated herein by reference.

TECHNICAL FIELD

This disclosure relates generally to balloons for performing medical procedures, such as angioplasty and, more particularly, to a radiopaque medical balloon.

BACKGROUND OF THE INVENTION

Balloon angioplasty is routinely used to remove blockages in the tubular organs such as arteries or veins. In many clinical situations, blockages are hard solids, such as calcified plaque, and require the use of high pressures to dislodge such blockages. Commercially available high pressure balloons employ complex technology to achieve high pressure requirements without sacrificing the profile of the balloon. Besides high pressure requirements, the angioplasty balloons also must be resistant to puncture and scratch, easy to track and push, and present a low profile.

In clinical practice, angioplasty balloons are inflated using an X-ray contrast agent solution. Typically, a 70/30 percent mixture of contrast agent and saline is used to inflate the balloon during an angioplasty procedure. Some large volume balloons sometimes require up to 2 minutes of inflation/deflation times with the contrast agent. In general, there is need to reduce inflation and deflation times required for angioplasty balloons without sacrificing the profile of the balloons.

Because of its relatively high viscosity, there is also a need to eliminate or reduce the use of contrast agent used in inflation/deflation of the balloons. Saline solution can be used in inflation and deflation; however, it has zero visibility in X-ray imaging. The use of contrast agent increases the cost of the procedure, prolongs the inflation/deflation times and also poses the risk of iodine exposure to patients who are sensitive to iodine. There is a need for compositions and methods, wherein inflation and deflation of angioplasty balloons can be achieved without the use of X-ray contrast agent.

Furthermore, the physician performing the angioplasty procedure should be able to locate the position of the uninflated balloon with accuracy, so that the balloon will be properly positioned during and after inflation. This is conventionally accomplished by attaching marker bands on the catheter shaft in the region corresponding to the balloon body, which requires additional components to be added to the catheter. Care must also be exercised to position such markers properly, and to secure them to the shaft by, for example, adhesive bonding or crimping. All of this adds to the cost of the catheter. Furthermore, once inflated, the balloon is typically imaged using contrast media, as described above.

Accordingly, the need is identified for a balloon with radiopacity associated with the balloon itself, which would accurately reveal the position of the balloon before inflation, as well as during and after inflation.

SUMMARY

One aspect of this disclosure is a radiopaque medical balloon for performing an angioplasty. In one embodiment, the balloon comprises a body including a non-complaint wall having an inner layer, an outer layer, and a discrete, intermediate layer at least partially between the inner and outer layer. The intermediate layer includes a film comprising a radiopaque material or a radiopaque foil.

The intermediate layer may comprise a pre-made film, and an adhesive may be provided for laminating the film to the inner or outer layer. The radiopaque material may comprise a metal, such as silver, platinum, gold, tin, indium, zirconium, bismuth, lead, cerium, rare earth metals, or alloys containing these elements. The material that is radiopaque may be dispersed within a polymer.

The outer layer of the balloon may comprise a thermoplastic or thermoset film. The film of the outer layer may be applied as a solution or dispersion. The outer layer may also comprise a radiopaque material.

A selected portion of the balloon may include the film, such as a cylindrical barrel portion or a conical portion. The film may have a first radiographic quality, and the balloon further includes a second radiopaque material having a second radiographic quality applied to a second portion of the balloon different from the first portion of the balloon. The second radiopaque material may be incorporated in a second film. The first radiopaque material may be present in an amount of up to about 65% by weight, and possibly at about 50% by weight. The second radiopaque material may be present in an amount of up to 65% by weight and about 43% by weight. The balloon may further include a third radiopaque material applied to the balloon, such as to the first and second portions.

A further aspect of this disclosure pertains to a medical balloon adapted for being inflated by an inflation fluid. The balloon has a radiopacity substantially from a first end to a second end in the absence of the inflation fluid. The radiopacity is provided at least in part by a foil or film layer.

The balloon may include an intermediate portion between the first end second ends, and the intermediate section has a first radiopacity that is different from a second radiopacity of another section of the balloon. The balloon may also include a barrel portion between conical end portions, the barrel portion having a first radiopacity that is different from a second radiopacity of one or both of the conical end portions. The foil or film layer may also be sandwiched between an inner layer of the balloon and an outer layer of the balloon.

Yet another aspect of this disclosure pertains to a medical balloon for performing an angioplasty. The medical balloon comprises a barrel portion including a first radiopaque foil or film, and a first cone portion including a second radiopaque foil or film. The balloon may further include a second cone portion having a third radiopaque foil or film, which may be the same as the second radiopaque foil or film.

Still another aspect of this disclosure is a method of forming a medical balloon, comprising providing a film including a radiopaque material between an inner layer of the balloon and an outer layer of a non-compliant wall of the balloon. The method may further include the step of forming the film, which in turn may involve mixing a polymer with a radiopaque material in the form of a powder and a solvent, and then drawing the mixture into a film. The film may comprise a first film having a first radiographic quality, and the providing step comprises providing the first film on a barrel or cone section of the balloon. The method may further include the step of applying a second material having a second radiographic quality to the other of the barrel or cone section of the balloon, which may be sprayed onto the balloon.

Another aspect of this disclosure relates to a method of forming a medical balloon adapted for being inflated by an inflation fluid. The method comprises, in the absence of an inflation fluid, providing the balloon with a radiopacity substantially from a first end to a second end, the radiopacity provided at least in part by a foil or film. The balloon may include an intermediate portion between the first end second ends, and the method may involve providing the intermediate section with a first radiopacity that is different from a second radiopacity of another section of the balloon. The balloon may include a barrel portion between conical end portions, and the method comprises providing the barrel portion having a first radiopacity that is different from a second radiopacity of one or both of the conical end portions. The method may further include the step of sandwiching the foil or film between an inner layer of the balloon and an outer layer of the balloon.

This disclosure may also related to a method of forming a radiopaque balloon, comprising the steps of forming a balloon body having a barrel section and cone sections at the ends; and at least partially covering one of the barrel section and the cone sections of the balloon body with a radiopaque film. The method may include the step of forming the radiopaque film into a generally rectangular sheet prior to the covering process, and/or bonding the radiopaque film to the balloon body (such as, for example, by adhesive bonding). The method may include the step of a working surface of the balloon with the radiopaque film.

Another aspect of the disclosure relates to a method of forming a device for performing an angioplasty procedure, comprising: providing a balloon body having a barrel section and cone sections at the ends, at least one of the barrel section and the cone sections of the balloon body being at least partially covered by a radiopaque film. The method may comprise the step of providing the radiopaque film covering only the barrel section, or providing the radiopaque film covering only the cone sections. The providing step may comprise providing the radiopaque film as the outermost layer of the device.

A further aspect of this disclosure relates to a method of forming an angioplasty balloon, comprising applying a radiopaque decal to an external surface of the balloon.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

MODES FOR CARRYING OUT THE INVENTION

The description provided below and in regard to the figures applies to all embodiments unless noted otherwise, and features common to each embodiment are similarly shown and numbered.

Figure 1:
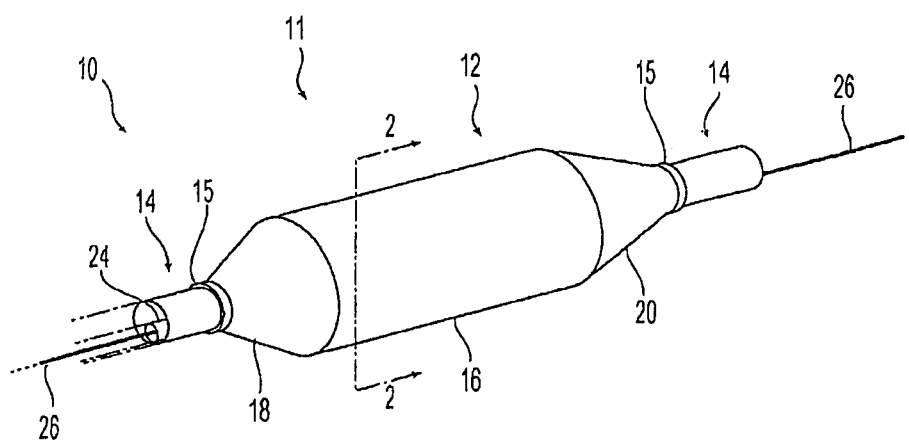
FIG. 1 is an isometric view of a portion of an exemplary catheter and of an exemplary balloon.
Figure 2:
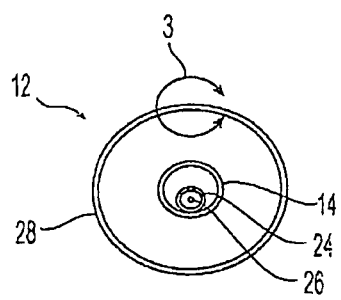
FIG. 2 is a cross-sectional view of the catheter and balloon of FIG. 1.

Provided is a catheter 10 having a distal portion 11 with a balloon 12 mounted on a catheter tube 14. Referring to FIGS. 1 and 2, the balloon 12 has an intermediate section 16, or "barrel," and end sections 18, 20 that reduce in diameter to join the intermediate section 16 to the catheter tube 14 (and thus sections 18, 20 are generally termed "cones"). The balloon 12 may be sealed at balloon ends 15 on the end sections 18, 20 to allow the inflation of the balloon 12 via one of more lumens extending within catheter tube 14 and communicating with the interior of the balloon. The catheter tube 14 also includes a guidewire lumen 24 that directs the passage of the guidewire 26 through the catheter 10.

Balloon 12 has a multi-layered balloon wall 28 forming the balloon 12, and may be a non-compliant balloon that has a balloon wall 28 that maintains its size and shape in one or more directions when the balloon is inflated. The balloon 12 may have a pre-determined surface area that remains constant during and after inflation, also has a pre-determined length and pre-determined circumference that each, or together, remain constant during and after inflation. However, the balloon may also be compliant or semi-compliant.

Figure 3:
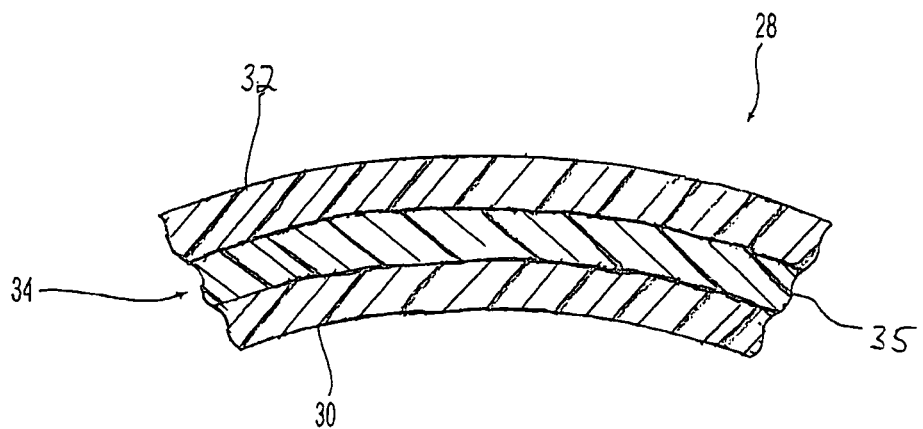
FIG. 3 is a cross-sectional view of a portion of the balloon of FIG. 1, and an enlarged view of a portion of the balloon of FIG. 2.
Figure 3A:
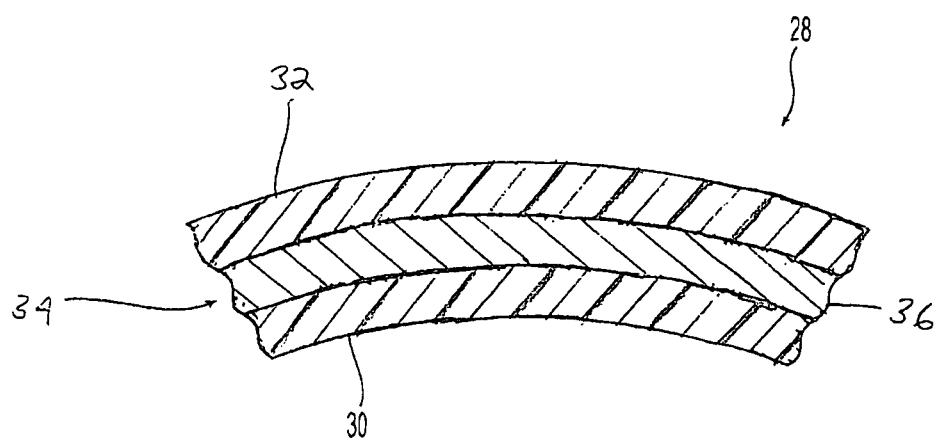
FIG. 3A is a cross-sectional view of a portion of the balloon including a radiopaque film.

The balloon 10 may have a radiopaque quality. This may be achieved along the intermediate section 16 by providing the balloon wall 28 comprising an inner layer 30 and an outer layer 32 sandwiching an intermediate layer 34 comprising a radiopaque film 35 (FIG. 3) or a foil (FIG. 3a). Alternatively, the film 35 or foil 36 may be provided only on the end sections 18, 20, which would appear the same as in FIGS. 2 and 3, except for the different diameter in cross-section. Additionally, the film 35 may be provided on both the intermediate section 16 and the end sections 18, 20, or one or both of these sections may instead be covered by a foil 36. In any case, the film 35 or foil 36 forming layer 34 may cover the entire circumference and length of the sections to which it is applied, but may be provided intermittently, if desired, so as to create portions of the balloon 10 with no radiopacity.

In one embodiment, the balloon 10 incorporates the film 35 or foil 36 in a manner that provides it with a radiographic quality substantially from a first end to a second end, even in the absence of an inflation fluid. This may be achieved by providing the intermediate section 16 with a first radiopacity, while one or both of the conical end sections 18, 20 have a second, different radiopacity. Such a result may be accomplished by providing a first material, such as a first film, having a first radiopacity on the intermediate section 16 and a second material, such as a second film, having the second, different radiopacity on the end sections 18, 20. When inserted into the desired location in the body and subjected to radiographic imaging (such as by using X-rays), this composite balloon 10 with differential radiographic qualities advantageously allows the observer to differentiate between the intermediate section 16 and the end sections 18, 20.

An adhesive may also be used to secure the outer layer 30 to the inner layer 32. This adhesive may secure or encapsulate the radiopaque film 35 or foil 36 of the intermediate layer 34 between these layers 30, 32. The adhesive may be a laminating adhesive such as a thermoplastic polyurethane, a thermoplastic acrylic, a rubber-based adhesive, a polyamide, polyvinyl acetate, a polyethylene-vinyl alcohol copolymer, a polyether-polyamide copolymer such as PEBAX, other solvent-borne adhesives, hot-melt adhesives, polyvinyl butyral, cellulosic derivatives such as cellulose-acetate-butyrate, silicone RTV's, or other similar flexible adhesives commonly employed to laminate films or bond plastic materials together. The adhesive may be a solvent borne adhesive of a flexible thermoplastic material, such as a polyurethane, polyamide or acrylic polymer. The adhesive in particular may be a thermoplastic polyurethane adhesive which can be applied as a solution, and re-activated with a solvent such as methyl ethyl ketone applied to the dried adhesive layer.

Alternatively, the adhesive can be a two-part adhesive, in which the two or more components are applied separately or as a pre-made mixture to the inner or outer layers that interact to form the adhesive. Examples include crosslinked polyurethanes, thermoset acrylic adhesives, epoxies, crosslinked polyureas, polyurethaneureas, two part silicone rubber adhesives, and other commonly employed two component adhesive materials. In yet another alternative, the adhesive base can be the reaction product of two substances. The adhesive may also be as shown and described in WO2010/027998, the disclosure of which is incorporated herein by this reference.

As noted above, radiopacity may be provided to the balloon 10 by the presence of a radiopaque film 35 or foil 36 as an intermediate layer 34 of the balloon wall 28. Radiopaque foils refer to metal foils produced from metals which exhibit a sufficiently high absorption of X-rays. Such foils should exhibit sufficient flexibility and malleability that they can be incorporated into the thin wall of a balloon 10, and provide the necessary flexibility, as would be experienced in folding and wrapping the balloon and subsequent deployment, unwrapping and inflation. Examples of such metal foils include, but are not limited to, thin foils made from, platinum, gold, silver, tin, copper, iridium, palladium, lead, and many other similar metals. Foils made from stiffer or brittle metals, such as tantalum or tungsten are not preferred, because the stiffness or brittleness would preclude their use in a thin balloon wall. Foils made from metals which do not significantly absorb X-rays; such as aluminum foil, can be used but are not preferred.

In particular, foils may include silver, gold and tin foils. Foil thickness must be sufficient to provide a desirable X-ray image. Optimum thickness will be determined by the metal used, the flexibility and balloon wall thickness requirements of the finished medical device, and the degree of imaging desired. Typically foils in the range of 2 to 40 microns work well, such as in the range of 8 to 20 microns. Foils may refer to solid thin sheets of metallic material. Alternatively, foils may be thin sheets of perforated or fibrous metal, or other forms of metal that can be formed into thin sheets.

Radiopaque films refer to preformed films of polymeric materials incorporating a radiopaque material or blend of Materials. Examples of such radiopopaque films include, but are not limited to, thermoplastic films including finely divided tungsten, tantalum, bismuth, bismuth trioxide, bismuth oxychloride, bismuth subcarbonate, other bismuth compounds, barium sulfate, tin, silver, silver compounds, rare earth oxides, and many other substances commonly used for X-ray absorption. The polymer used for making these films may be any polymeric material which can be loaded with radiopacifier and formed into a sufficiently thin film. Examples of film polymers include thermoplastic and thermoset polymers. Some examples of thermoplastic polymers include, but are not limited to, polyurethanes, polyamides, polyether-polyamide copolymers such as PEBAX, polyethylene terephthalate or other polyesters, polyvinyl acetate, polyvinyl chloride, and many other thermoplastic materials useful for making films. Some examples of thermoset polymers include, but are not limited to, crosslinked polyurethanes, polyureas, epoxies, acrylics, silicones, and many other thermoset materials that can be formed into thin films.

Figure 4A:
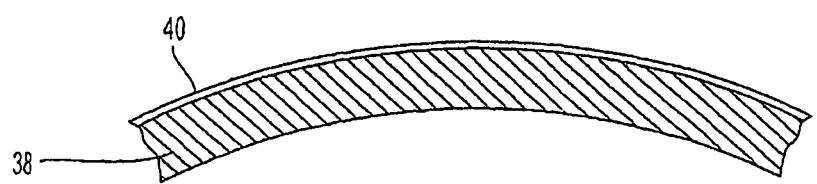
FIGS. 4A-4B are cross-sectional views illustrating the manufacture of another embodiment of a balloon.

One particular embodiment of the present invention is to form the radiopaque film in situ by applying a solvent solution or dispersion directly to a base balloon, which solution or dispersion consists of the film-forming polymer, the finely divided radiopaque agent, and the solvent. As shown in FIG. 4A, such a solution or dispersion could be applied to a base balloon 38 by brushing, spraying, dipping, or other means, to produce a thin radiopaque film 40, prior to adding a laminating adhesive and outer layer 32, which may comprise a protective film or other coating.

Figure 4B:
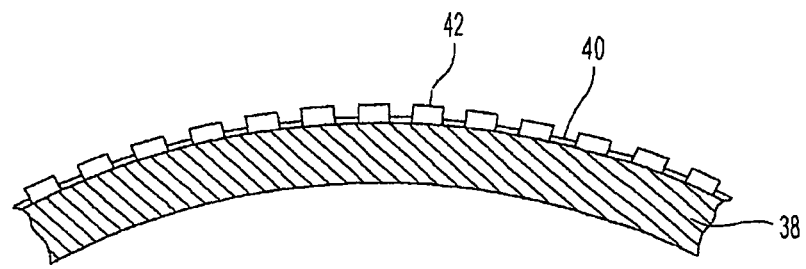

As shown in FIG. 4B, it may be desirable to add reinforcing fibers or filaments 42 to increase the balloon strength under pressure. If reinforcing fibers are included, an adhesive layer may be used to laminate the fibers into this layer, before the foil or film 35 is applied. The fibers 42 may comprise any high strength fibers or filaments that impart the desired properties to the balloon. Examples of suitable fibers include, but are not limited to, ultrahigh molecular weight polyethylene such as SPECTRA or DYNEEMA fibers, polyamide fibers, polyimide fibers, ultrahigh molecular weight polyurethane fibers such as TECHNORA, fibers made from polyesters, polypropylene, or other polymers known in the art, or finely drawn strands of metals, such as stainless or high tensile steel. The fibers may also comprise a radiopaque material.

Several layers of fibers may be used, oriented in different directions. In such case, the first layer of fibers may be ultra-high molecular weight polyurethane or TECHNORA fibers having a diameter of about 12 microns that have been flattened to a rectangular profile of about 0.0005 of an inch by 0.020 of an inch. The first fibers may be disposed in a longitudinal direction on the base balloon to form a longitudinal fiber layer extending the longitudinal length of the central section and/or the longitudinal length of the entire balloon. Adhesive may be added before a second layer of fibers is applied. If so, one possible orientation is to wrap these fibers helically about the circumference of the balloon, so that these fibers overly and encapsulate the underlying radiopaque film or foil and the first layer of fibers.

The outer layer 32 may provide abrasion resistance when forming the exterior and acts to consolidate or secure the radiopaque film 35 or foil 36 within the balloon wall. This surface layer 32 may comprise a thermoplastic or thermoset material applied as a film, or it can be applied as a thermoset or thermoplastic solution or dispersion which forms a protective film during lamination. Examples of protective film materials include, but are not limited to polyesters, polyamide, polyamide-polyether block copolymers, polyurethanes, ionomers such as SURLYN, polyethylene, polypropylene, crosslinkable materials such as polyurethanes or polyethylene, and many other film materials commonly employed in the lamination art. The protective film may be one which melts and fuses at the temperatures used for subsequent lamination, or it may be one which does not melt. A polyether block copolymer, such as PEBAX, may be used. The protective film may also include some radiopaque material dispersed within the film material, to impart additional radiopacity.

Figure 5:
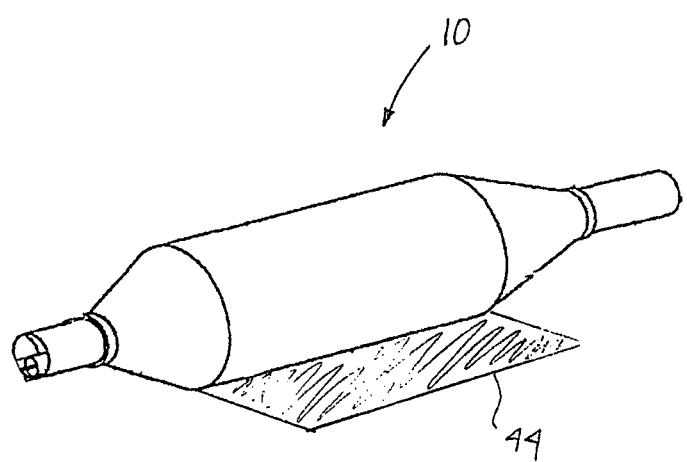
FIG. 5 is a perspective view of a balloon being provided with a radiopaque film as an outer layer.

The outer layer 32 may also comprise a radiopaque film, such as for example a radiopaque appliqué or decal 44 attached to the balloon 10, which may otherwise be formed of non-radiopaque materials. For instance, a radiopaque film comprised of 40-50 vol % of Tungsten or Bismuth trioxide in a polymer matrix. More specifically, a low melting polymer such as polycaprolactone or certain polyurethanes could be dissolved in solvent. Radiopacifier may then be milled into the solution, to produce a mix which could be drawn down into a thin radiopaque film, and dried. The film could be cut into a shape, such as a rectangle, of appropriate size and applied to the balloon 10, as shown in FIG. 5, which would then be heat-laminated to the outside surface of the balloon under heat and pressure. The decal would stick to the balloon surface by hot-melt adhesion, or an adhesive could be optionally added during the lamination process (polycaprolactone in particular has a low melting point and good hot-melt adhesion). The radiopaque decal 44 may also take other forms of shapes, such as for covering only a portion of the balloon 10 (such as a longitudinal strip along the working surface, a frusto-conical shape for covering one or more of the cone or end sections 18, 20, a strip for extending circumferentially over a portion of the barrel section 16, or random sizes or shapes to delineate the location of any desired portion of the balloon under fluoroscopy).

To form outer layer 32, a protective coating may be used instead of or in addition to a film material, such as for example thermoset or thermoplastic solutions or dispersions. Examples of thermoset or thermoplastic solutions or dispersions which form a protective film during lamination for abrasion resistance include, but are not limited to, epoxies, polyurethanes, polyesters, alkyd resins, polyvinylbutyral, cellulose nitrate, polyvinyl acetate, phenolic resins such as phenol-formaldehyde resins, amino resins such as amino-formaldehyde resins, and many other coating materials commonly employed in the art. The coating may also include some radiopaque material dispersed within it, to impart additional radiopacity.

Good adhesion to the inner layer 30, which as noted above may be the wall of a base balloon 38, can be achieved with many laminating adhesives. However, the surface of the layer 30 may be chemically or physically modified to further improve the adhesion of the adhesive to the balloon surface. For example, various adhesion improving coatings or treatments, generally known in the coating art as "primers" could be used to improve the adhesion of the adhesive. Surface modification methods such chemical etching with acids, plasma surface modification and the like may also improve the adhesion of the adhesive.

In order to consolidate the laminated structure, it may be desirable to provide the appropriate conditions to intimately bond and fuse the inner, adhesive, fibers (if present) and outer (e.g., protective film) components. The composite materials of the balloon 10 may be heated in a die using heat and pressure to fuse these materials into a consolidated structure. If the adhesive is a thermoplastic material, such as a polyurethane, the heat will soften the adhesive and cause it to flow and bond to the balloon, fibers (if present), and protective film. If the adhesive contains a catalyst, or is a 2-part material that requires reaction of the two components in order to cure, the heat provides the means to accelerate the cure process.

As can be appreciated, the present balloon 10 in the described embodiments may afford several advantages. Providing an internal radiopaque film 35 or foil 36 provides the advantage of improved abrasion protection of the radiopaque layer, since it is effectively encapsulated between the balloon and an outer protective film. Another advantage is the potential to use a much thicker layer of radiopaque material, which can allow better visibility of the balloon under X-ray, than would be possible with an ink, sputtered or vacuum deposited film, or a topical coating. Also the risk of debonding or flaking during folding and inflation is greatly reduced or eliminated, since the foil or film is encapsulated. A further advantage is the potential for less costly and simpler processing, since relatively simple techniques may be employed for applying and laminating the adhesive, foil or film, and outer protective film.

Using foils or films, all or portions of the balloon may be inherently radiopaque, which potentially avoids the need to rely on a significant radiopacity contribution from the inflation fluid. Therefore, this fluid may have a minimal concentration of radiopaque material (which may be in the form of a fluid). The inflation fluid more may have a concentration of radiopaque fluid that is from 0% (pure saline) to approximately 40%, or in range of approximately 0-20%, possibly in a range of approximately 0-5%, and may contain no radiopaque fluid at all.

Generally, radiopaque fluids have a viscosity that is greater than the viscosity of pure physiological saline. Likewise, it is believed that mixtures of saline with radiopaque fluids have viscosities that are less than undiluted radiopaque fluid but still greater than the viscosity of pure saline. The greater viscosities of radiopaque fluids and saline/radiopaque fluid mixtures thus cause such fluid to move, at a given pressure, more slowly through tubing than the movement of pure saline under the same conditions. The greater viscosities of radiopaque fluids, compared to pure saline, thus require greater head pressures to push the radiopaque fluids through tubing, and greater head pressures to achieve the balloon inflation times achieved with saline under the same conditions. The relatively higher viscosities of radiopaque fluids thus cause the balloon to fill more slowly as compared to a balloon inflated with pure saline, which increases the time and/or effort required to complete a medical procedure involving the use of a balloon and radiopaque imaging, and an increase in the time required to achieve balloon inflation or deflation, as shown in Table 1.

Table 1 shows the effect of contrast agent concentration on deflation time of a Conquest balloon:

| Percent Contrast | Deflation Time (Sec) (average and stdev) |
| --- | --- |
| 5 | 5 ± 0 |
| 10 | 5.5 ± 0.7 |
| 20 | 6 ± 0 |
| 30 | 6 ± 0 |
| 40 | 7 ± 0 |
| 50 | 8.5 ± 0.7 |

Thus, the increase in contrast concentration leads to significant increase in deflation time. However, low concentration, such as >30%, 5 to 20% concentration, or 5-10 percent contrast agent may be used without significantly sacrificing the deflation times.

The balloon 10 with the radiopaque film 35 or foil 36 would also enhance the visibility in the compressed state (see FIG. 5). This improves the ability of the clinician to track the balloon during advancing the balloon into the patient, and also facilitates removing the balloon during clinical use.

Since a radiopaque balloon could be inflated with normal saline with a low viscosity or other non-radiopaque fluids, including gases (such as carbon dioxide), it would be easier to ensure complete deflation in the patient after dilatation. A fully deflated balloon is less likely to encounter issues when the balloon is being removed through the introducer, helping to ensure a safer procedure.

EXAMPLES

Certain of the foregoing concepts are illustrated by the following examples, which are not to be considered as limiting the scope of the disclosure.

Example 1

Polyethylene terephthalate (PET) angioplasty balloons, measuring 12 mm in diameter, and with a double wall thickness of approximately 0.002 inches were mounted on appropriate mandrels to allow balloons to be inflated. The inflated balloons were sprayed with a 5 wt % solution of a polyurethane laminating adhesive available as Tecoflex 1-MP Adhesive so that a uniform quantity of adhesive covered the balloons. The adhesive rapidly dried on the surface of the balloon.

Six strips of annealed silver metal foil were prepared, measuring 1.5 mm wide, 30 mm long and approximately 7.5 microns thick. Annealed silver was chosen as a metal which is both soft and flexible, is biocompatible, and has good X-ray absorption properties. These strips were applied to the body of the balloon by moistening the adhesive on the surface of the balloon with a brush containing a small amount of methyl ethyl ketone (MEK) solvent. The strips were placed in the axial orientation about the middle portion of the 12 mm diameter body of the balloon, evenly spaced about the circumference.

Two additional strips of silver metal foil were prepared, measuring 1.5 mm wide, 35 mm long and approximately 7.5 microns thick. These strips were placed circumferentially about the balloon body, in the region near the body/cone transition, to delineate the edges of the 12 mm diameter portion of the body of the balloon.

A thin layer of additional laminating adhesive solution was then sprayed onto the balloon to cover the balloon surface and the foil strips.

The balloon surface was then wrapped circumferentially with a 50 denier yarn composed of ultrahigh molecular weight polyethylene (UHMWPE), commercially available as SPECTRA yarn. The yarn was applied at a pitch of approximately 50 threads per inch. The balloon, thus wrapped, was then sprayed with additional radiopaque adhesive.

The balloons were then wrapped helically with a thin strip of polyether-polyamide copolymer film, commercially available as PEBAX. The film thickness with a thickness of approximately 0.0005 inches was stretched during wrapping to further reduce the thickness. Once wrapped, the balloons were placed in laminating dies of an appropriate size and shape to allow heat and pressure to be applied to the balloon surface. Balloons were heated to a temperature of approximately 220 F with pressure applied to the surface of the balloon, for a sufficient period of time to cause the radiopaque laminating adhesive to flow and consolidate the balloon and PEBAX film.

The result was a laminated angioplasty balloon with embedded foil strips delineating the 12 mm portion of the body of the balloon. The balloons exhibited excellent flexibility, and could be wrapped and folded and unwrapped, without any issues. Balloons were examined by X-ray, and showed excellent visibility, without the need to fill them with contrast media. By comparison, conventional PET balloons, and fiber reinforced angioplasty balloons of the same size did not exhibit a visible image under X-ray.

Example 2

Polyethylene terephthalate (PET) angioplasty balloons, measuring 12 mm in diameter, and with a double wall thickness of approximately 0.002" were processed as described above, but using annealed silver foil with a thickness of 12 microns. Balloons continued to exhibit excellent flexibility. Visibility under X-ray was better than the balloons in example 1, as expected, due to the thicker foil.

Example 3

Polyethylene terephthalate (PET) angioplasty balloons, measuring 12 mm in diameter, and with a double wall thickness of approximately 0.002" were processed as described above, but using annealed silver foil with a thickness of 20 microns. Balloons continued to exhibit excellent flexibility. Visibility under X-ray was better than the balloons in examples 1 and 2, as expected, due to the thicker foil.

Example 4

Polyethylene terephthalate (PET) angioplasty balloons, measuring 12 mm in diameter, and with a double wall thickness of approximately 0.002" were processed as described above, but using tin foil with a thickness of 12 microns. Tin was chosen as metal which is soft and flexible, biocompatible, and having good X-ray absorption properties.

Balloons exhibited excellent flexibility, as well as good visibility under X-ray.

Comparative Example 5

Polyethylene terephthalate (PET) angioplasty balloons, measuring 12 mm in diameter, and with a double wall thickness of approximately 0.002" were processed as described above, but using a tantalum foil with a thickness of 25 microns. Tantalum is a metal which is biocompatible, and has good X-ray absorption properties.

In contrast to Examples 1-4 above, these balloons were more limited in terms of flexibility due to the stiffness of the tantalum foil.

Comparative Example 6

Polyethylene terephthalate (PET) angioplasty balloons, measuring 12 mm in diameter, and with a double wall thickness of approximately 0.002" were processed as described above, but using annealed aluminum foil with a thickness of 25 microns. Annealed aluminum is a metal which is biocompatible, and has good flexibility.

These balloons exhibited excellent flexibility, and could be wrapped and folded and unwrapped, without any issues.

However, in contrast to Examples 1-4 above, these balloons lacked the necessary radiopacity to show up well under X-ray.

Examples 5 and 6 illustrate the desirability for the radiopaque foils or films to exhibit both flexibility and radiopacity.

Example 7

A radiopaque film forming formulation was prepared by adding the following components into a plastic mixing container:
22.4 grams of a thermoplastic polyesterurethane laminating adhesive available as Estane 5701 F1P.
224 grams N,N-Dimethylacetamide
153 grams of tungsten powder, submicron size These components were mixed together briefly, then placed in a glass jar, and rolled slowly for 24 hours to dissolve the Estane. The mix was then transferred into a laboratory ball mill jar charged with aluminum oxide ceramic balls. The jar was then rolled on a ball mill roller for 24 hours to reduce the particle size of the Tungsten, after which the mixture was removed from the ball mill, filtered and stored in a glass container. The result was a homogeneous composition of approximately 44 wt % solids.

Thin films of this liquid formulation were then formed on a clean glass plate, by drawing down the liquid onto the glass using a draw down blade set to 0.010", so that the wet film thickness was 0.010". The wet film was then dried in an oven at 140 F for 1 hour. The result was a thin flexible film, measuring approximately 0.001" thick. The composition of this film was approximately 30 vol % Tungsten, and 70 vol % polyurethane.

Polyethylene terephthalate (PET) angioplasty balloons, measuring 12 mm in diameter, and with a double wall thickness of approximately 0.002" were mounted on appropriate mandrels to allow balloons to be inflated. The inflated balloons were sprayed with a 5 wt % solution of a polyurethane laminating adhesive available as TECOFLEX 1-MP adhesive so that a uniform quantity of adhesive covered the balloons. The adhesive rapidly dried on the surface of the balloon.

For each balloon two strips of the above prepared film were cut, measuring 10 mm wide and 35 mm long. These strips were applied to the body of the balloon by moistening the adhesive on the surface of the balloon with a brush containing a small amount of methyl ethyl ketone (MEK) solvent. These strips were placed circumferentially about the balloon body, in the region near the body/cone transition, to delineate the end regions of the 12 mm diameter portion of the body of the balloon.

The balloon surface was then wrapped circumferentially with a 50 denier SPECTRA yarn, at a pitch of approximately 50 threads per inch. The balloon, thus wrapped, was then sprayed with additional adhesive.

The balloons were then wrapped helically with a thin strip of PEBAX film as described in Example 1, and laminated in a die under heat and pressure.

The result was a laminated angioplasty balloon with embedded radiopaque strips delineating the end regions of the 12 mm portion of the body of the balloon. The balloons exhibited excellent flexibility, and could be wrapped and folded and unwrapped, without any issues. Balloons were examined by X-ray, and showed excellent visibility, without the need to fill them with contrast media.

Example 8

A radiopaque film forming formulation was prepared by adding the following components into a plastic mixing container:
26.4 grams of a thermoplastic polyester urethane laminating adhesive available as ESTANE 5701 F1P
262 grams N,N-Dimethylacetamide
1118 grams of Bismuth Trioxide powder These components were mixed together briefly, then placed in a glass jar, and rolled slowly for 24 hours to dissolve the ESTANE. The mix was then transferred into a laboratory ball mill jar charged with aluminum oxide ceramic balls. The jar was then rolled on a ball mill roller for 24 hours to reduce the particle size of the Bismuth Trioxide, after which the mixture was removed from the ball mill, filtered and stored in a glass container. The result was a homogeneous composition of approximately 34.5 wt % solids.

Thin films of this liquid formulation were then formed on a clean glass plate, by drawing down the liquid onto the glass using a draw down blade set to 0.010", so that the wet film thickness was 0.010". The wet film was then dried in an oven at 140 F for 1 hour. The result was a thin flexible film, measuring approximately 0.001" thick. The composition of this film was approximately 36.5 vol % Bismuth Trioxide, and 63.5 vol % polyurethane.

Two strips of this film were cut and applied to each balloon, as described in Example 7. The balloons were then processed as described in Example 7.

The result was a laminated angioplasty balloon with embedded radiopaque strips delineating the end regions of the 12 mm portion of the body of the balloon. The balloons exhibited excellent flexibility, and could be wrapped and folded and unwrapped, without any issues. Balloons were examined by X-ray, and showed excellent visibility, without the need to fill them with contrast media.

Example 9

A radiopaque film forming mixture was prepared by combining the following ingredients:
2326 grams of a thermoplastic laminating adhesive formulation commercially available as product 1-MP from Lubrizol Corp.
3100 grams of Tungsten metal powder, approximate particle size range of 1-5 microns.
The result is a mixture which, when cast and dried, yields a dried film with a composition that contains 50 volume % Tungsten.

Example 10

A radiopaque film forming mixture was prepared by combining the following ingredients:
2625 grams of a thermoplastic laminating adhesive formulation commercially available as product 1-MP from Lubrizol, Corp.
2453 grams of Bismuth Trioxide powder.
The result is a mixture which, when cast and dried, yields a dried film with a composition that contains 60 volume % Bismuth Trioxide.

Example 11

A radiopaque film forming mixture was prepared by combining the following ingredients:

2760 grains of a thermoplastic laminating adhesive formulation commercially available as product 1-MP from Lubrizol Corp.

1299 grams of Bismuth Trioxide powder.

The result is a mixture which, when cast and dried, yields a dried film with a composition that contains 43 volume % Bismuth Trioxide.

Example 12

A radiopaque adhesive mixture was prepared by combining the following ingredients:

1266 grams of a thermoplastic laminating adhesive formulation commercially available as product 1-MP from Lubrizol, Corp.

1467 grams of Bismuth Trioxide powder.

697 grams of Methyl Ethyl Ketone 427 grams of Acetone 1163 grams of Propylene glycol monomethyl ether acetate;

The result is a mixture which, when dried, yields a dried film with a composition that contains 65 volume % Bismuth Trioxide.

To experiment with the differential but substantially continuous radiopacity, the following balloons were constructed having intermediate layers 34 including the following materials (approximately):

A. 50% Tungsten drawn with a 10 mil blade on barrel with 43% Bismuth Trioxide drawn with 10 mil blade on both cones.

B. 65% Bismuth Trioxide drawn with a 10 mil blade on barrel with 43% Bismuth Trioxide drawn with 10 mil blade on both cones.

C. 50% Tungsten drawn w/7 mil blade on barrel with 43% Bismuth Trioxide drawn w/10 mil blade on both cones.

D. 50% Tungsten drawn with 10 mil blade on barrel with 43% Bismuth Trioxide drawn with 10 mil blade on both cones and 65% Bismuth Trioxide spray applied to cones and barrel.

E. 65% Bismuth Trioxide drawn with 10 mil blade on barrel, 43% Bismuth Trioxide drawn with 10 mil blade on both cones in cone, and 65% Bismuth Trioxide spray applied to cones and barrel.

F. 50% Tungsten drawn with 7 mil blade on barrel, 43% Bismuth Trioxide drawn with 10 mil blade on both cones, and 65% Bismuth Trioxide spray applied to cones and barrel.

G. 50% Tungsten drawn with 10 mil blade on barrel with natural 1 mp in cones and 65% Bismuth Trioxide spray applied to cones and barrel.

H. 65% Bismuth Trioxide drawn with 10 mil blade on barrel with natural 1 mp in cones and 65% Bismuth Trioxide spray on cones and barrel.

I. 50% Tungsten drawn with 7 mil blade on barrel with natural 1 mp in cones and 65% Bismuth Trioxide spray on cones and barrel.

Figure 6:
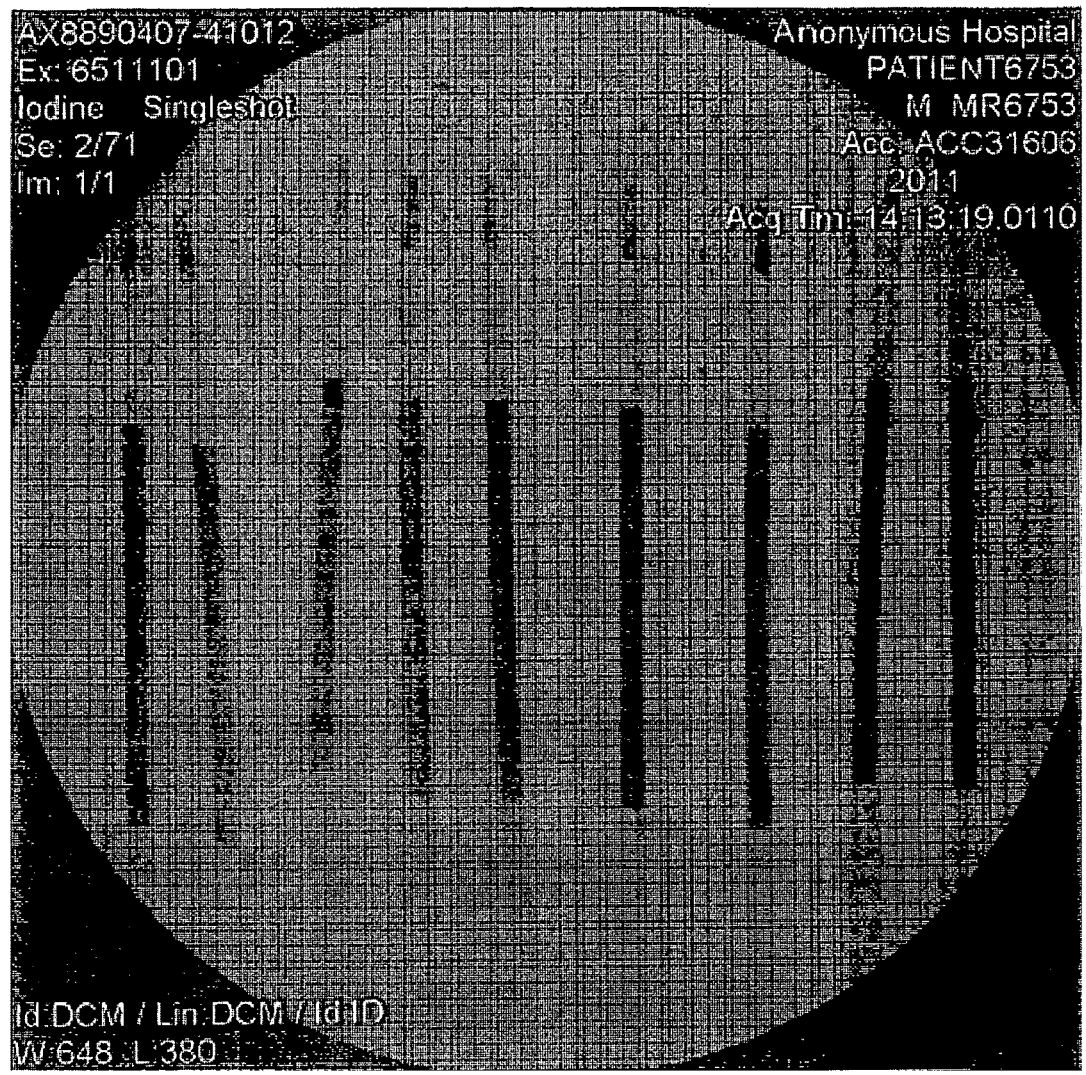
FIGS. 6-10 are radiographic images of balloons, including those made according to this disclosure.
Figure 7:
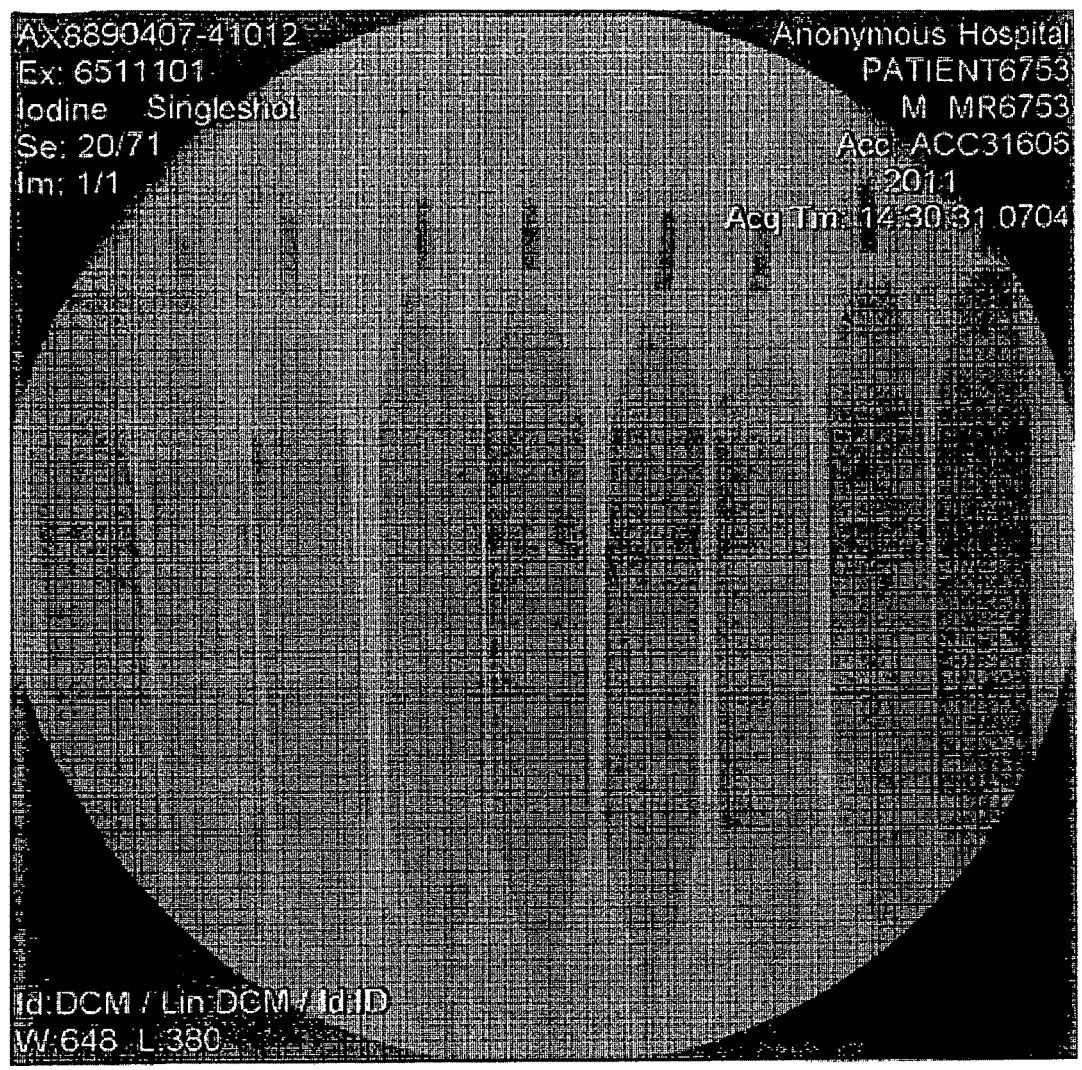
Figure 8:
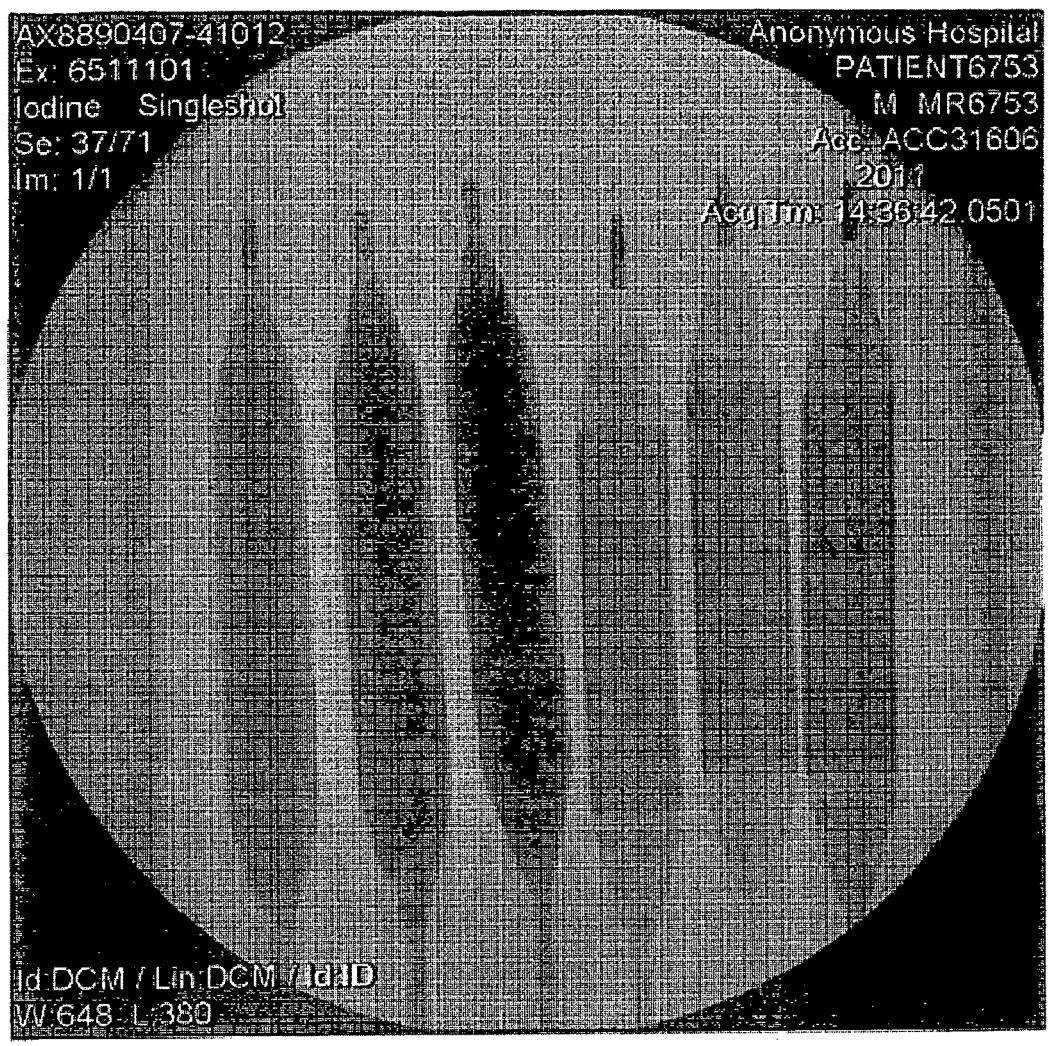
Figure 9:
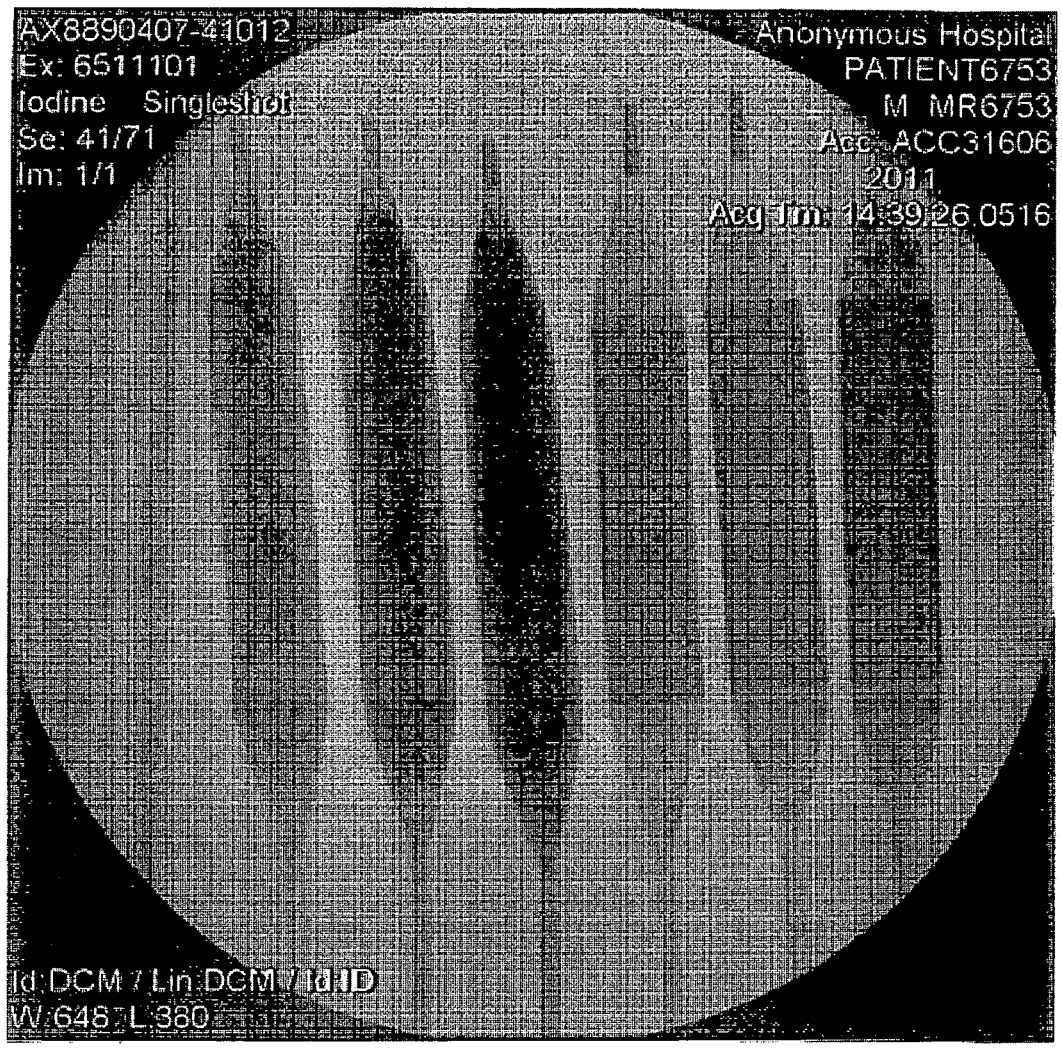
Figure 10:
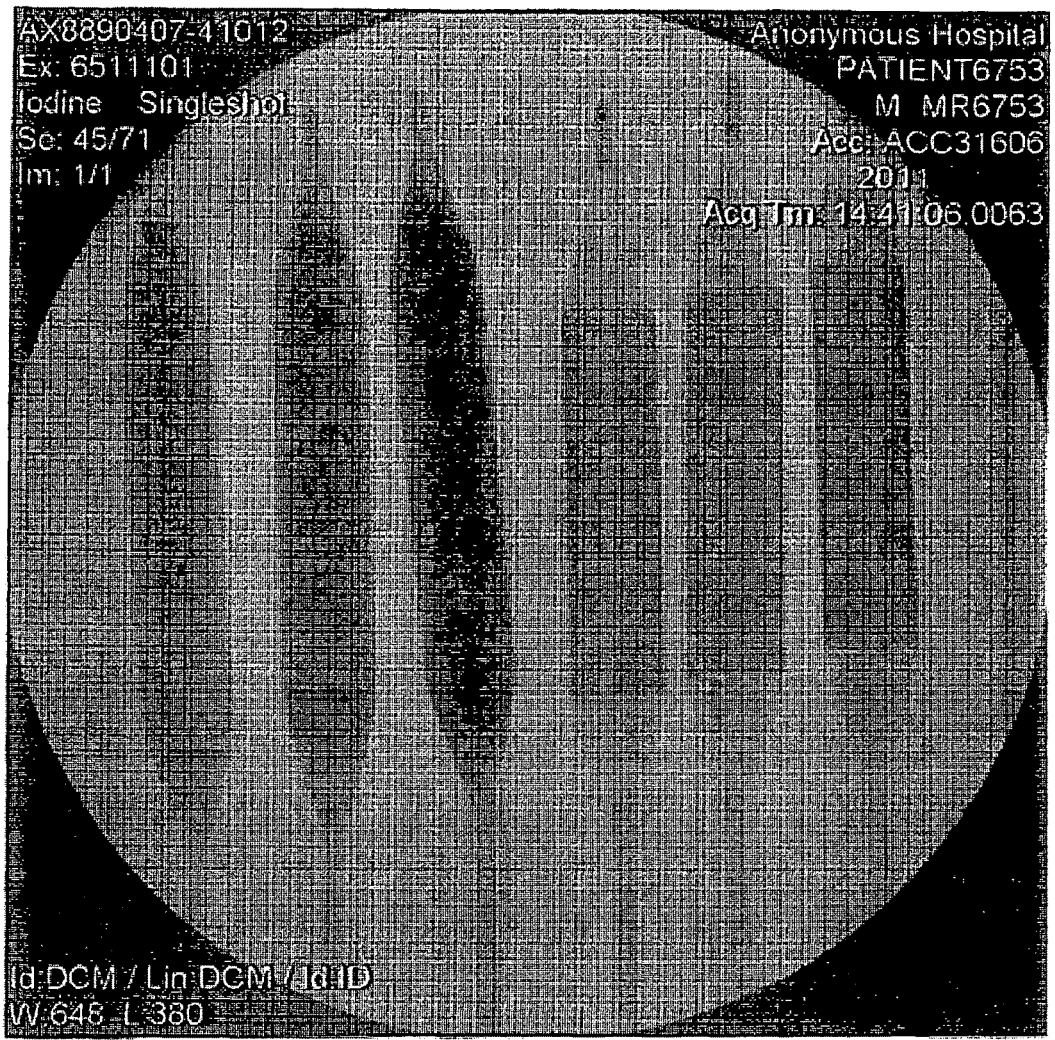

FIGS. 6-10 comprise radiographic images of these embodiments. FIGS. 6 and 7 illustrate the above-mentioned embodiments A-I, both folded and unfolded. In FIGS. 8, 9, and 10, the first three balloons preceding the samples (A-C in FIG. 8; D-F in FIG. 9; and G-I in FIG. 10) are control samples that consist of 80/20, 70/30, 50/50 contrast to saline ratio, while the radiopaque balloons in each image are inflated with 100% saline. Not only can the differential radiopacity been seen from these figures, but also the contrast provided between different sections of the radiographic balloon, which helps the physician to identify the contours during an interventional procedure, both prior to inflation and thereafter.

Summarizing, the disclosure pertains to the following items:

1. A non-compliant medical balloon for performing an angioplasty, comprising:
   a body including a non-compliant wall having an inner layer, an outer layer, and a discrete, intermediate layer at least partially between the inner and outer layer, the intermediate layer including a film comprising a radiopaque material.

2. The balloon of item 2, further including an adhesive for laminating the film to the inner or outer layer.

3. The balloon of item 1 or 2, wherein the radiopaque material comprises a metal.

4. The balloon of any of the preceding items, wherein the radiopaque material is selected from the group consisting of silver, platinum, gold, tin, indium, zirconium, bismuth, lead, cerium, rare earth metals, or alloys containing these elements.

5. The balloon of any of the preceding items, wherein the film comprises a polymer in which the radiopaque material is dispersed.

6. The balloon of any of the preceding items, wherein the outer layer comprises a thermoplastic film.

7. The balloon of any of the preceding items, wherein the outer layer comprises a thermoset film.

8. The balloon of any of the preceding items, wherein the outer layer comprises a thermoplastic material applied as a solution or dispersion.

9. The balloon of any of the preceding items, wherein the outer layer comprises a thermoset material applied as a solution or dispersion.

10. The balloon of any of the preceding items, wherein a selected first portion of the balloon includes the film.

11. The balloon of item 10, wherein the selected first portion comprises a cylindrical barrel portion of the balloon.

12. The balloon of item 10 or 11, wherein the selected first portion comprises a conical portion of the balloon.

13. The balloon of any of the preceding items 10 to 12, wherein the film has a first radiographic quality defined by a first radiopaque material in the first portion, and further including a second radiopaque material applied to a second portion of the balloon different from the first portion of the balloon.

14. The balloon of item 13, wherein the second radiopaque material is incorporated in a second film.

15. The balloon of item 13 or 14, wherein the first radiopaque material is present in an amount of up to about 65% by weight.

16. The balloon of any of the preceding items 13 to 15, wherein the first radiopaque material is present in an amount of about 50% by weight.

17. The balloon of any of the preceding items 13 to 16, wherein the second radiopaque material is present in an amount of up to about 65% by weight.

18. The balloon of any of the preceding items 13 to 17, wherein the second radiopaque material is present in an amount of about 43% by weight.

19. The balloon of any of the preceding items 13 to 18, further including a third radiopaque material applied to the balloon.

20. The balloon of item 19, wherein the third radiographic material is applied to the first and second portions of the balloon.

21. The balloon of any of the preceding items, wherein one or more of the layers includes a fiber.
22. The medical balloon of any of the preceding items, adapted for being inflated by an inflation fluid, said balloon having a radiopacity substantially from a first end to a second end in the absence of the inflation fluid, said radiopacity provided at least in part by a foil or film layer.
23. The medical balloon of item 22, wherein the balloon includes an intermediate portion between the first end and second end, and the intermediate section has a first radiopacity that is different from a second radiopacity of another section of the balloon.
24. The medical balloon of item 22 or 23, wherein the balloon includes a barrel portion between conical end portions, the barrel portion having a first radiopacity that is different from a second radiopacity of one or both of the conical end portions.
25. The medical balloon of any of the preceding items 22 to 24, wherein the foil or film layer is sandwiched between an inner layer of the balloon and an outer layer of the balloon.
26. The medical balloon of any of the preceding items for performing an angioplasty, comprising:
    a barrel portion including a first radiopaque foil or film; and
    a first cone portion including a second radiopaque foil or film.
27. The balloon of item 26, further including a second cone portion having a third radiopaque foil or film.
28. The balloon of item 27, wherein the second radiopaque foil or film and the third radiopaque foil or film are the same.

The following items also relate to the invention:
1. A non-compliant medical balloon for performing an angioplasty, comprising:
    a body including a non-compliant wall having an inner layer, an outer layer, and a discrete, intermediate layer at least partially between the inner and outer layer, the intermediate layer including a film comprising a radiopaque material.
2. The balloon of item 2, further including an adhesive for laminating the film to the inner or outer layer.
3. The balloon of item 1 or 2, wherein the radiopaque material comprises a metal.
4. The balloon of any of the preceding items, wherein the radiopaque material is selected from the group consisting of silver, platinum, gold, tin, indium, zirconium, bismuth, lead, cerium, rare earth metals, or alloys containing these elements.
5. The balloon of any of the preceding items, wherein the film comprises a polymer in which the radiopaque material is dispersed.
6. The balloon of any of the preceding items, wherein the outer layer comprises a thermoplastic film.
7. The balloon of any of the preceding items, wherein the outer layer comprises a thermoset film.
8. The medical balloon of any of the preceding items for performing an angioplasty, comprising:
    a body including a non-compliant wall having an inner layer, an outer layer, and a discrete, intermediate layer at least partially between the inner and outer layer, the intermediate layer including a film comprising a radiopaque material.
9. The balloon of item 8, further including an adhesive for laminating the film to the inner or outer layer.
10. The balloon of item 8 or 9, wherein the radiopaque material comprises a metal.
11. The balloon of any of the preceding items 8 to 10, wherein the radiopaque material is selected from the group consisting of silver, platinum, gold, tin, indium, zirconium, bismuth, lead, cerium, rare earth metals, or alloys containing these elements.
12. The balloon of any of the preceding items 8 to 11, wherein the film comprises a polymer in which the radiopaque material is dispersed.
13. The balloon of any of the preceding items 8 to 12, wherein the outer layer comprises a thermoplastic film.
14. The balloon of any of the preceding items 8 to 13, wherein the outer layer comprises a thermoset film.
15. The balloon of any of the preceding items 8 to 14, wherein the outer layer comprises a thermoplastic material applied as a solution or dispersion.
16. The balloon of any of the preceding items 8 to 15, wherein the outer layer comprises a thermoset material applied as a solution or dispersion.
17. The balloon of any of the preceding items 8 to 16, wherein a selected first portion of the balloon includes the film.

The following items also relate to the invention:
1. A medical balloon for performing an angioplasty, comprising:
    a barrel portion including a first radiopaque foil or film; and
    a first cone portion including a second radiopaque foil or film.
2. The balloon of item 1, further including a second cone portion having a third radiopaque foil or film.
3. The balloon of item 2, wherein the second radiopaque foil or film and the third radiopaque foil or film are the same.
4. The medical balloon of any of the preceding items for performing an angioplasty, comprising:
    a body including a non-compliant wall having an inner layer, an outer layer, and a discrete, intermediate layer at least partially between the inner and outer layer, the intermediate layer including a film comprising a radiopaque material.
5. The balloon of item 4, further including an adhesive for laminating the film to the inner or outer layer.
6. The balloon of item 4 or 5, wherein the radiopaque material comprises a metal.
7. The balloon of any of the preceding items 4 to 6, wherein the radiopaque material is selected from the group consisting of silver, platinum, gold, tin, indium, zirconium, bismuth, lead, cerium, rare earth metals, or alloys containing these, elements.
8. The balloon of any of the preceding items 4 to 7, wherein the film comprises a polymer in which the radiopaque material is dispersed.
9. The balloon of any of the preceding items 4 to 8, wherein the outer layer comprises a thermoplastic film.
10. The balloon of any of the preceding items 4 to 9, wherein the outer layer comprises a thermoset film.
11. The balloon of any of the preceding items 4 to 10, wherein the outer layer comprises a thermoplastic material applied as a solution or dispersion.
12. The balloon of any of the preceding items 4 to 11, wherein the outer layer comprises a thermoset material applied as a solution or dispersion.
13. The balloon of any of the preceding items 4 to 12, wherein a selected first portion of the balloon includes the film.
14. The balloon of item 13, wherein the selected first portion comprises a cylindrical barrel portion of the balloon.

15. The balloon of item 13 or 14, wherein the selected first portion comprises a conical portion of the balloon.
16. The balloon of any of the preceding items 13 to 15, wherein the film has a first radiographic quality defined by a first radiopaque material in the first portion, and further including a second radiopaque material applied to a second portion of the balloon different from the first portion of the balloon.
17. The balloon of item 16, wherein the second radiopaque material is incorporated in a second film.
18. The balloon of item 16 or 17, wherein the first radiopaque material is present in an amount of up to about 65% by weight.
19. The balloon of any of the preceding items 16 to 18, wherein the first radiopaque material is present in an amount of about 50% by weight.
20. The balloon of any of the preceding items 16 to 19, wherein the second radiopaque material is present in an amount of up to about 65% by weight.
21. The balloon of any of the preceding items 16 to 20, wherein the second radiopaque material is present in an amount of about 43% by weight.
22. The balloon of any of the preceding items 16 to 21, further including a third radiopaque material applied to the balloon.
23. The balloon of item 22, wherein the third radiographic-material is applied to the first and second portions of the balloon.
24. The balloon of any of the preceding items 4 to 23, wherein one or more of the layers includes a fiber:
25. The medical balloon any of the preceding items adapted for being inflated by an inflation fluid, said balloon having a radiopacity substantially from a first end to a second end in the absence of the inflation fluid, said radiopacity provided at least in part by a foil or film layer.
26. The medical balloon of item 25, wherein the balloon includes an intermediate portion between the first end and second end, and the intermediate section has a first radiopacity that is different from a second radiopacity of another section of the balloon.
27. The medical balloon of item 25 or 26, wherein the balloon includes a barrel portion between conical end portions, the barrel portion having a first radiopacity that is different from a second radiopacity of one or both of the conical end portions.
28. The medical balloon of any of the preceding items 25 to 27, wherein the foil or film layer is sandwiched between an inner layer of the balloon and an outer layer of the balloon.
29. A method of forming a medical balloon, comprising:
providing a film including a first radiopaque material between an inner layer and an outer layer of a non-compliant wall of the balloon.
30. The method of item 29, further including the step of forming the film.
31. The method of item 30, wherein the forming step comprises mixing a polymer with a radiopaque material in the form of a powder and a solvent.
32. The method of item 31, further including the step of drawing the mixture into a film.
33. The method of any of the preceding items 29 to 32, wherein the film comprises a first film having a first radiographic quality, and the providing step comprises providing the first film on a barrel or cone section of the balloon.
34. The method of item 33, further including the step of applying a second film having a second radiographic quality to the other of the barrel or cone section of the balloon.
35. The method of item 33 or 34, further including the step of spraying a second radiopaque material onto the balloon.
36. A method of forming a medical balloon according to any of the preceding items 29 to 35 adapted for being inflated by an inflation fluid, comprising:
in the absence of an inflation fluid, providing the balloon with a radiopacity substantially from a first end to a second end, said radiopacity provided at least in part by a foil or film.
37. The method of item 36, wherein the balloon includes an intermediate portion between the first and second ends, and the method includes providing the intermediate section with a first radiopacity that is different from a second radiopacity of another section of the balloon.
38. The method of item 36 or 37, wherein the balloon includes a barrel portion between conical end portions, and the method comprises providing the barrel portion having a first radiopacity that is different from a second radiopacity of one or both of the conical end portions.
39. The method of any of the preceding items 36 to 38, further including the step of sandwiching the foil or film between an inner layer of the balloon and an outer layer of the balloon.

The following items also relate to the invention:
1. A medical balloon for performing an angioplasty, comprising:
a barrel portion including a first radiopaque foil or film; and
a first cone portion including a second radiopaque foil or film.
2. The balloon of item 1, further including a second cone portion having a third radiopaque foil or film.
3. The balloon of item 2, wherein the second radiopaque foil or film and the third radiopaque foil or film are the same.
4. The medical balloon of any of the preceding items for performing an angioplasty, comprising:
a body including a non-compliant wall having an inner layer, an outer layer, and a discrete, intermediate layer at least partially between the inner and outer layer, the intermediate layer including a film comprising a radiopaque material.
5. The balloon of item 4, further including an adhesive for laminating the film to the inner or outer layer.
6. The balloon of item 4 or 5, wherein the radiopaque material comprises a metal.
7. The balloon of any of the preceding items 4 to 6, wherein the radiopaque material is selected from the group consisting of silver, platinum, gold, tin, indium, zirconium, bismuth, lead, cerium, rare earth metals, or alloys containing these elements.
8. The balloon of any of the preceding items 4 to 7, wherein the film comprises a polymer in which the radiopaque material is dispersed.
9. The balloon of any of the preceding items 4 to 8, wherein the outer layer comprises a thermoplastic film.
10. The balloon of any of the preceding items 4 to 9, wherein the outer layer comprises a thermoset film.
11. The balloon of any of the preceding items 4 to 10, wherein the outer layer comprises a thermoplastic material applied as a solution or dispersion.

12. The balloon of any of the preceding items 4 to 11, wherein the outer layer comprises a thermoset material applied as a solution or dispersion.
13. The balloon of any of the preceding items 4 to 12, wherein a selected first portion of the balloon includes the film.
14. The balloon of item 13, wherein the selected first portion comprises a cylindrical barrel portion of the balloon.
15. The balloon of item 13 or 14, wherein the selected first portion comprises a conical portion of the balloon.
16. The balloon of any of the preceding items 13 to 15, wherein the film has a first radiographic quality defined by a first radiopaque material in the first portion, and further including a second radiopaque material applied to a second portion of the balloon different from the first portion of the balloon.
17. The balloon of item 16, wherein the second radiopaque material is incorporated in a second film.
18. The balloon of item 16 or 17, wherein the first radiopaque material is present in an amount of up to about 65% by weight.
19. The balloon of any of the preceding items 16 to 18, wherein the first radiopaque material is present in an amount of about 50% by weight.
20. The balloon of any of the preceding items 16 to 19, wherein the second radiopaque material is present in an amount of up to about 65% by weight.
21. The balloon of any of the preceding items 16 to 20, wherein the second radiopaque material is present in an amount of about 43% by weight.
22. The balloon of any of the preceding items 16 to 21, further including a third radiopaque material applied to the balloon.
23. The balloon of item 22, wherein the third radiographic material is applied to the first and second portions of the balloon.
24. The balloon of any of the preceding items 4 to 23, wherein one or more of the layers includes a fiber.
25. The medical balloon any of the preceding items adapted for being inflated by an inflation fluid, said balloon having a radiopacity substantially from a first end to a second end in the absence of the inflation fluid, said radiopacity provided at least in part by a foil or film layer.
26. The medical balloon of item 25, wherein the balloon includes an intermediate portion between the first end and second end, and the intermediate section has a first radiopacity that is different from a second radiopacity of another section of the balloon.
27. The medical balloon of item 25 or 26, wherein the balloon includes a barrel portion between conical end portions, the barrel portion having a first radiopacity that is different from a second radiopacity of one or both of the conical end portions.
28. The medical balloon of any of the preceding items 25 to 27, wherein the foil or film layer is sandwiched between an inner layer of the balloon and an outer layer of the balloon.
29. A method of forming a medical balloon adapted for being inflated by an inflation fluid, comprising:
    in the absence of an inflation fluid, providing the balloon with a radiopacity substantially from a first end to a second end, said radiopacity provided at least in part by a foil or film.
30. The method of item 29, wherein the balloon includes an intermediate portion between the first and second ends, and the method includes providing the intermediate section with a first radiopacity that is different from a second radiopacity of another section of the balloon.
31. The method of item 29 or 30, wherein the balloon includes a barrel portion between conical end portions, and the method comprises providing the barrel portion having a first radiopacity that is different from a second radiopacity of one or both of the conical end portions.
32. The method of any of the preceding items 29 to 31, further including the step of sandwiching the foil or film between an inner layer of the balloon and an outer layer of the balloon.
33. The method of forming the medical balloon of any of the preceding items 29 to 32, comprising:
    providing a film including a first radiopaque material between an inner layer and an outer layer of a non-compliant wall of the balloon.
34. The method of item 33, further including the step of forming the film.
35. The method of item 34, wherein the forming step comprises mixing a polymer with a radiopaque material in the form of a powder and a solvent.
36. The method of item 35, further including the step of drawing the mixture into a film.
37. The method of any of the preceding items 33 to 36, wherein the film comprises a first film having a first radiographic quality, and the providing step comprises providing the first film on a barrel or cone section of the balloon.
38. The method of item 37, further including the step of applying a second film having a second radiographic quality to the other of the barrel or cone section of the balloon.
39. The method of item 37 or 38, further including the step of spraying a second radiopaque material onto the balloon.

Another item comprises a non-compliant medical balloon for performing an angioplasty, comprising:
    a body including a barrel section with cone sections at the opposite ends; and
    a radiopaque film forming an outer covering along one of the barrel section or the cone sections.

The film may be applied as a decal or appliqué to an external surface of the body, and may cover either the barrel section or the cone sections, but possibly not both the barrel section and the cone sections. Alternatively, the externally applied film may have the differential radiopacity among the various sections of the balloon (e.g., one radiopacity on the barrel section, and a different radiopacity on the cone sections).

While the disclosure presents certain embodiments to illustrate the inventive concepts, numerous modifications, alterations, and changes to the described embodiments are possible without departing from the sphere and scope of the present invention, as defined in the appended claims. For example, the ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Accordingly, it is intended that the present invention not be limited to the described embodiments, but that it has the full scope defined by the language of the following claims, and equivalents thereof.

The invention claimed is:

1. A non-compliant medical balloon for performing an angioplasty, comprising:
a body including a non-compliant wall having an inner layer, an outer layer, and a discrete, intermediate layer at least partially between the inner and outer layer, at least the intermediate layer comprising a film including a radiopaque material.

2. The balloon of claim 1, further including an adhesive for laminating the film to the inner or outer layer.

3. The balloon of claim 1, wherein the film comprises a polymer in which the radiopaque material is dispersed.

4. The balloon of claim 1, wherein the outer layer comprises a thermoplastic film.

5. The balloon of claim 1, wherein the outer layer comprises a thermoset film.

6. The balloon of claim 1, wherein the outer layer comprises a thermoplastic material applied as a solution or dispersion.

7. The balloon of claim 1, wherein the outer layer comprises a thermoset material applied as a solution or dispersion.

8. The balloon of claim 1, wherein the film is provided on a first portion of the balloon.

9. The balloon of claim 8, wherein the first portion is a cylindrical barrel portion of the balloon.

10. The balloon of claim 8, wherein the first portion is a conical portion of the balloon.

11. The balloon of claim 8, wherein the film is a first film having a first radiographic quality, and further including a second radiopaque material applied to a second portion of the balloon different from the first portion of the balloon.

12. The balloon of claim 11, wherein the second radiopaque material is incorporated in a second film.

13. The balloon of claim 12, wherein the first film comprises a strip of film.

14. The balloon of claim 11, wherein the first radiopaque material is present in an amount of up to 65% by volume of the film.

15. The balloon of claim 11, wherein the first radiopaque material is present in an amount of about 50% by volume of the film.

16. The balloon of claim 11, wherein the second radiopaque material is present in an amount of up to 65% by volume of the film.

17. The balloon of claim 11 wherein the second radiopaque material is present in an amount of about 43% by volume of the film.

18. The balloon of claim 11, further including a third radiopaque material applied to the balloon.

19. The balloon of claim 18, wherein the third radiopaque material is applied to the first and second portions of the balloon.

* * * * *